United States Patent
Stark

(10) Patent No.: US 8,183,872 B2
(45) Date of Patent: May 22, 2012

(54) HOSE WITH FAULT DETECTION CAPABILITY

(75) Inventor: Jason Dennis Stark, Temperance, MI (US)

(73) Assignee: Eaton Corporation, Cleveland, OH (US)

( * ) Notice: Subject to any disclaimer, the term of this patent is extended or adjusted under 35 U.S.C. 154(b) by 316 days.

(21) Appl. No.: 12/499,477

(22) Filed: Jul. 8, 2009

(65) Prior Publication Data

US 2010/0007325 A1   Jan. 14, 2010

Related U.S. Application Data

(60) Provisional application No. 61/079,245, filed on Jul. 9, 2008.

(51) Int. Cl.
*G01R 31/02* (2006.01)
(52) U.S. Cl. .............. 324/539; 73/40.5 R; 73/49.5
(58) Field of Classification Search ............ 174/11 R; 324/539, 661; 73/49.5, 40.5 R, 780, 772; 138/104, 127; 340/604; 702/34
See application file for complete search history.

(56) References Cited

U.S. PATENT DOCUMENTS

| | | | | | |
|---|---|---|---|---|---|
| 4,029,889 | A | * | 6/1977 | Mizuochi | 174/11 R |
| 5,267,670 | A | | 12/1993 | Foster | |
| 5,343,738 | A | * | 9/1994 | Skaggs | 73/40.5 R |
| 5,551,484 | A | * | 9/1996 | Charboneau | 138/104 |
| 5,634,497 | A | * | 6/1997 | Neto | 138/127 |
| 5,969,618 | A | * | 10/1999 | Redmond | 340/604 |
| 5,992,218 | A | * | 11/1999 | Tryba et al. | 73/40.5 R |
| 6,386,237 | B1 | * | 5/2002 | Chevalier et al. | 138/104 |
| 6,498,991 | B1 | * | 12/2002 | Phelan et al. | 702/34 |
| 6,958,615 | B2 | * | 10/2005 | Poulbot et al. | 324/661 |
| 2003/0164048 | A1 | * | 9/2003 | Shkel | 73/780 |
| 2004/0065377 | A1 | | 4/2004 | Whiteley | |
| 2006/0196252 | A1 | * | 9/2006 | Deckard | 73/49.5 |
| 2007/0051166 | A1 | * | 3/2007 | Baker et al. | 73/40.5 R |
| 2007/0131035 | A1 | | 6/2007 | Krutz et al. | |

FOREIGN PATENT DOCUMENTS

| | | |
|---|---|---|
| DE | 3140804 A1 | 4/1983 |
| WO | 2008001238 A2 | 1/2008 |

OTHER PUBLICATIONS

Hewlett Packard Technical Manual (See attached).*
Hewlett Packard Technical Manual (See attached), printed on Apr. 24, 2003.*

* cited by examiner

*Primary Examiner* — Roberto Velez
*Assistant Examiner* — Temilade S Rhodes-Vivour
(74) *Attorney, Agent, or Firm* — Quinn Law Group, PLLC

(57) ABSTRACT

A hose fault detection system includes a hose assembly and a fault detector. The hose assembly includes a first conductive layer, second conductive layer, and an intermediate layer that is disposed between the first and second conductive layers. Each of the first and second conductive layers has an electrical characteristic. The fault detector is configured for detecting an electrical change based on the electrical characteristic to signify a potential impending failure of at least one of the first and second conductive layers of the hose. The fault detector includes a sensing device, a recording device and a digital processor. The sensing device is in electrical communication with the first and second conductive layers to measure the electrical characteristic. The recording device is configured for storing the measured electrical characteristic.

14 Claims, 7 Drawing Sheets

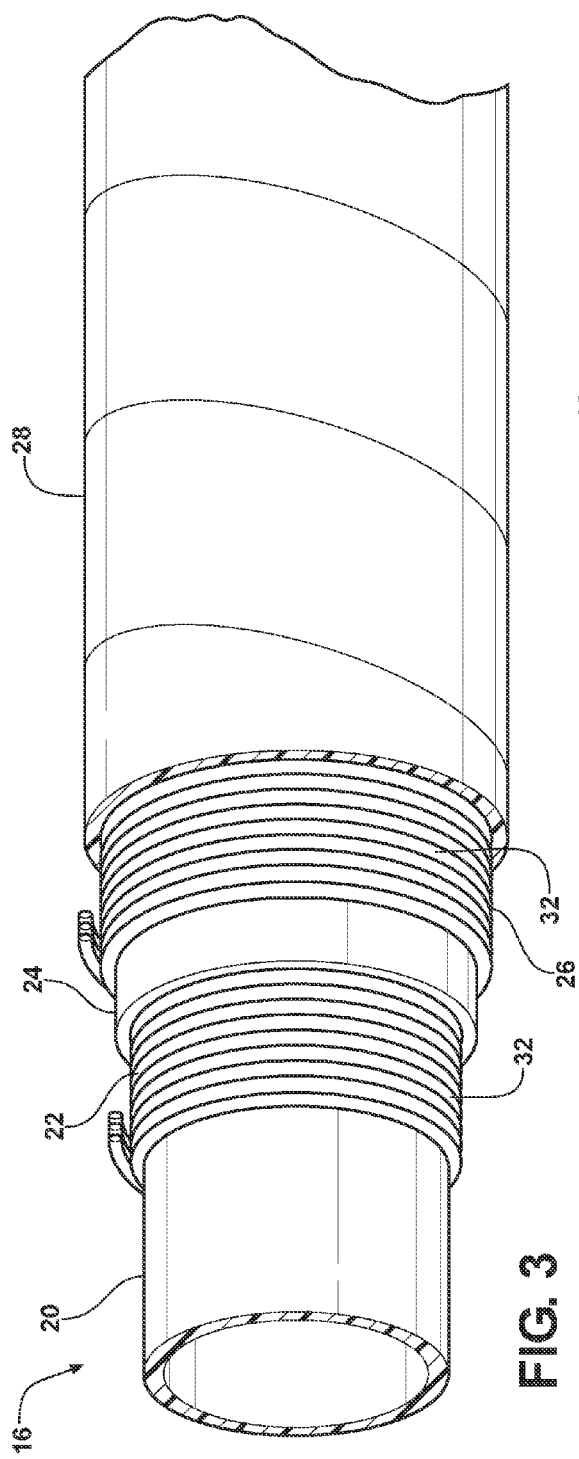
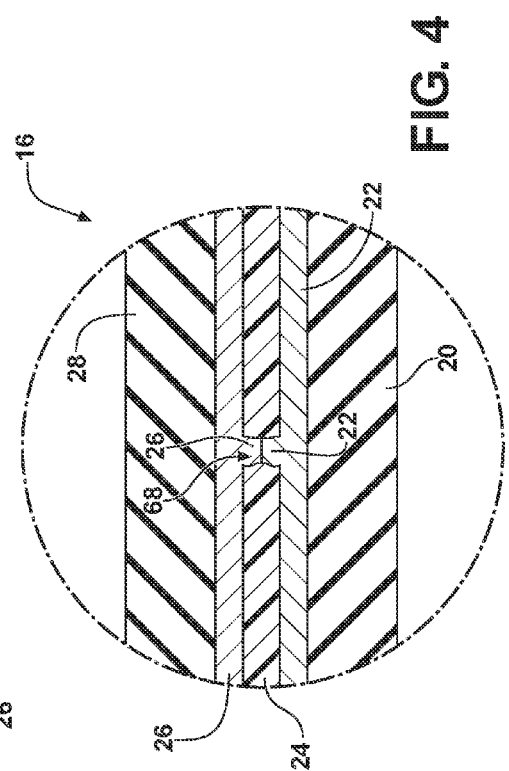
FIG. 3
FIG. 4

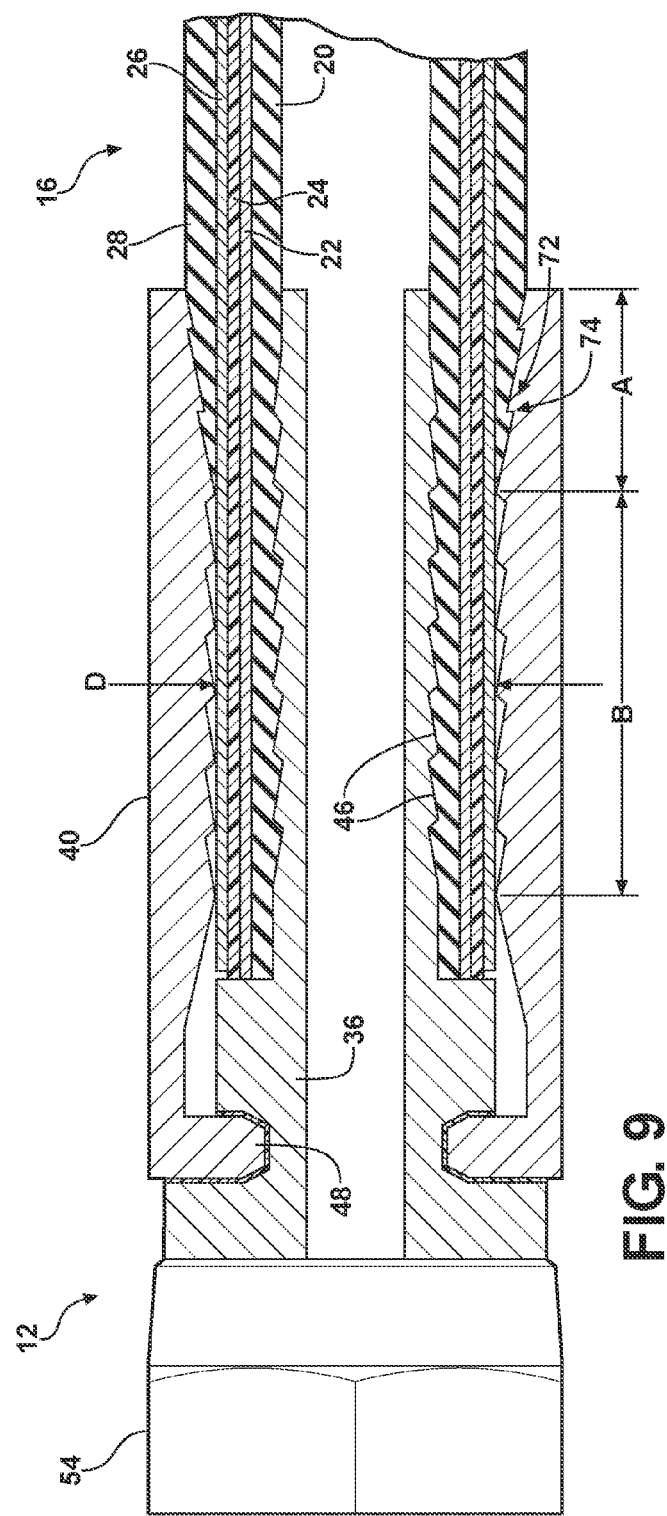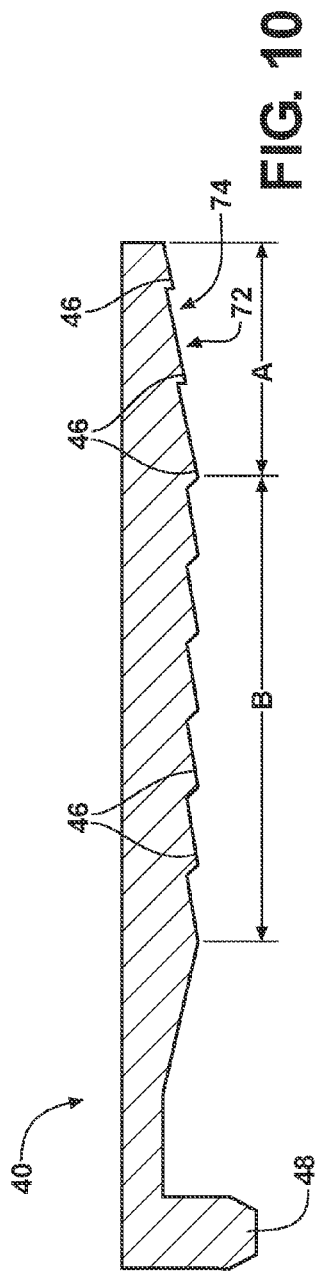

HOSE WITH FAULT DETECTION CAPABILITY

CROSS-REFERENCE TO RELATED APPLICATIONS

This application claims the benefit of U.S. Provisional Application 61/079,245, filed Jul. 9, 2008, and which is hereby incorporated by reference in its entirety.

TECHNICAL FIELD

The present invention relates to a hose with fault detection capability.

BACKGROUND

High pressure reinforced hydraulic hose is typically used on a variety of fluid power operated machines, such as earthmoving machines, to provide a flexible connection between several moving parts of a hydraulic circuit employed on or within the machine. Such hoses may include a hollow polymeric inner tube on which successive cylindrical layers of reinforcing material, such as wire or textile, are concentrically applied to contain the radial and axial pressures developed within the inner tube. Many applications require hose constructions with both high burst strength and long term fatigue resistance. Using conventional technology, the burst strength of a hose design may be increased by adding additional reinforcing material and/or layers, a practice which is generally discouraged because of its negative impact on the flexibility of the hose, or by universally increasing the tensile strength of each layer of reinforcement material, which may come at the expense of hose fatigue resistance. To determine the robustness of a hose design, a hose manufacturer typically performs, among other tests, an impulse test and a burst test on the hose. An impulse test measures a hose design's resistance to fatigue failure by cyclically subjecting the hose to hydraulic pressure. A burst test, on the other hand, is a destructive hydraulic test employed to determine the ultimate strength of a hose by uniformly increasing internal pressure until failure. Based on these and other tests, a manufacturer can estimate a hose life that can be used to determine when a hose has reached the end of its life and may require replacing.

SUMMARY OF THE INVENTION

A hose fault detection system includes a hose and a fault detector. The hose includes at least one conductive layer with an electrically conductive characteristic. The fault detector is electrically connected to the conductive layer and is configured for detecting an electrical change based on the electrically conductive characteristic to signify a potential impending failure of the hose.

In another embodiment, a hose fault detection system includes a hose assembly and a fault detector. The hose assembly includes a first conductive layer, second conductive layer, and an intermediate layer that is disposed between the first and second conductive layers. Each of the first and second conductive layers has an electrical characteristic. The fault detector is configured for detecting an electrical change based on the electrical characteristic to signify a potential impending failure of at least one of the first and second conductive layers of the hose. The fault detector includes a sensing device, a recording device and a digital processor. The sensing device is in electrical communication with the first and second conductive layers to measure the electrical characteristic. The recording device is configured for storing the measured electrical characteristic.

In yet another aspect of the invention, a hose fault detection system includes a hose assembly and a fault detector. The hose assembly includes a first conductive layer, a second conductive layer, a socket, and a nipple. Each of the first and second conductive layers has an electrical characteristic. The socket is in electrical communication with the second conductive layer. The nipple is in electrical communication with the first conductive layer. The fault detector is configured for detecting an electrical change based on the electrical characteristic to signify a potential impending failure of at least one of the first and second conductive layers of the hose. The fault detector includes a sensing device, a first lead wire, and a second lead wire. The sensing device is configured to measure the electrical characteristic between the first and second conductive layers. The first lead wire electrically interconnects the sensing device and the socket. The second lead wire electrically interconnects the sensing device and the nipple.

The above features and advantages and other features and advantages of the present invention are readily apparent from the following detailed description of the best modes for carrying out the invention when taken in connection with the accompanying drawings.

BRIEF DESCRIPTION OF THE DRAWINGS

Referring now to the figures, which are exemplary embodiments and wherein like elements are numbered alike:

FIG. 3 is a perspective view, partially cut away, illustrating the exemplary hose employing a spiral wire reinforcement layer;

FIG. 4 is an exploded cross-sectional view of the exemplary hose illustrating a fault occurring within an intermediate layer of the hose;

FIG. 9 is a partial cross-sectional view of yet another exemplary hose of FIG. 1 employing a modified socket and nipple; and FIG. 10 is a partial cross-sectional view of the socket of the hose fitting of FIG. 9.

DETAILED DESCRIPTION

Figure 1:
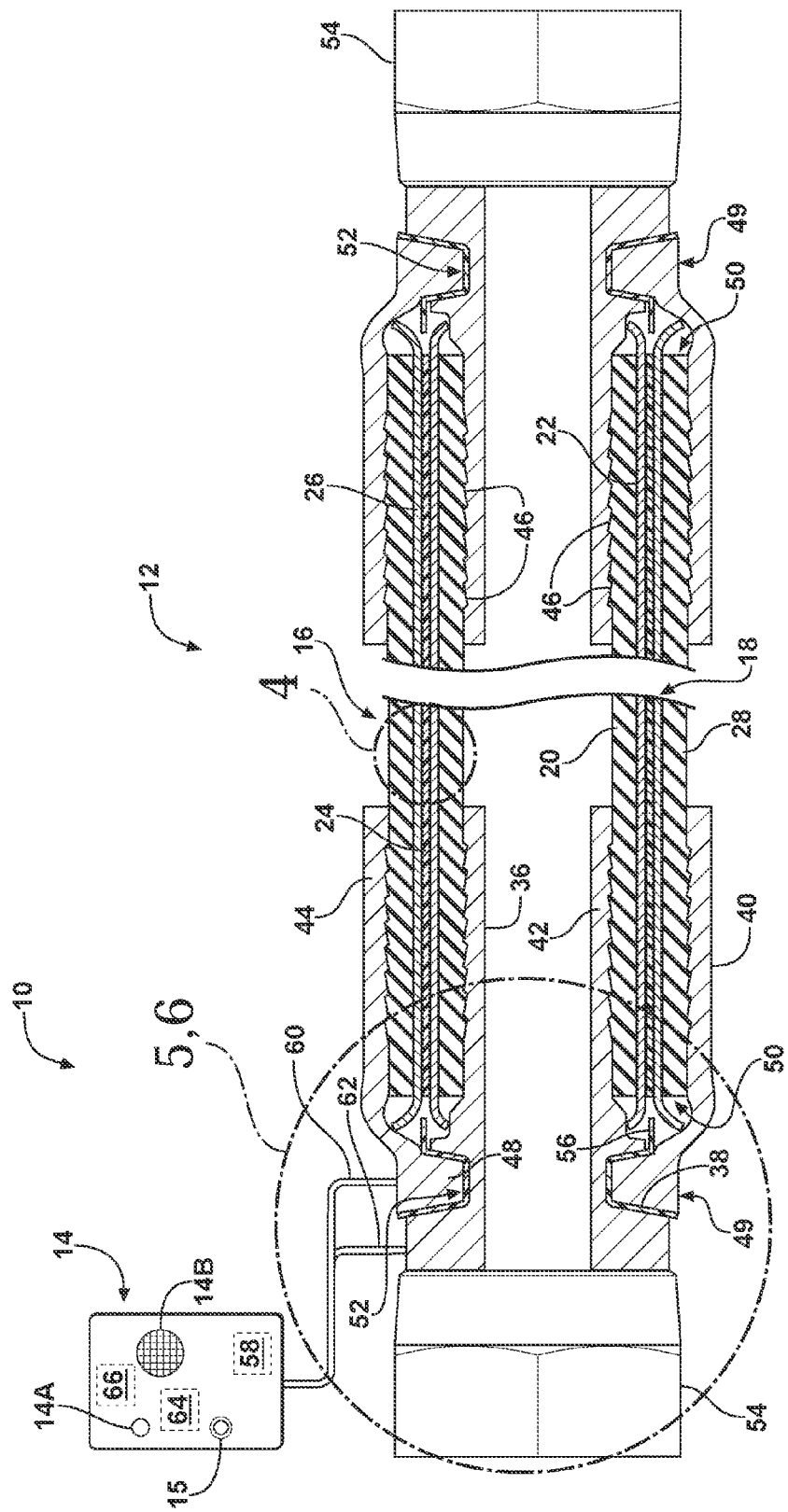
FIG. 1 is a partial cross-sectional view of an exemplary hose employing a fault detection system.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the disclosed device. Further, the descriptions set forth herein are not intended to be exhaustive or otherwise limit or restrict the claims to the precise forms and configurations shown in the drawings and disclosed in the following detailed description.

Referring to FIG. 1, an exemplary hose fault detection system 10 is shown to include a hose assembly 12 and a fault detector 14 electrically connected to the hose assembly 12. The hose assembly 12 includes a generally flexible hose 16 having a multi-layer construction 18. The hose structure may include an inner tube 20 made from a polymeric material, such as rubber or plastic, or another material depending on the requirements of the particular application. A first conductive layer 22 having at least one electrically conductive characteristic overlays the inner tube 20 and an intermediate layer 24 overlays the first conductive layer 22. A second conductive layer 26 having at least one electrically conductive characteristic overlays the intermediate layer 24. The first and second conductive layers 22, 26 may be configured as a reinforcing layer. An outer cover 28 may overlay the second conductive layer 26, and may include, for example, an extruded layer (not shown) of rubber or plastic. The outer cover 28 may itself include a reinforcing layer (not shown).

The intermediate layer 24 operates to at least partially insulate electrically the first and second conductive layers 22, 26 from one another. The intermediate layer 24 may have any of a variety of constructions. For example, the intermediate layer 24 may include a single layer of an electrically resistive material. The intermediate layer 24 may also include multiple layers, wherein at least one of the layers exhibits electrical insulating properties. Certain composite materials may also be employed in the intermediate layer 24, such as a woven fabric bonded to a polymeric material. Composite materials having various other constructions may also be utilized. Composite materials may also be used in combination with other materials to form the intermediate layer 24.

The conductive layers 22, 26 generally extend the entire length and span the entire circumference of the hose 16. This is generally the case when the conductive layer 22, 26 also functions as a reinforcement layer. The intermediate layer 24 may also extend over the entire length and circumference of the hose 16. There may be instances, however, where at least one of the conductive layers 22, 26 extends only over a portion of the hose 16 length and/or a portion of the hose 16 circumference. In those instances, the intermediate layer 24 may also be configured to generally extend over the region of the hose 16 containing the partial conductive layer 22, 26. The partial intermediate layer 24 may be positioned within the hose 16 so as to separate the conductive layers 22, 26 from one another.

Figure 2:
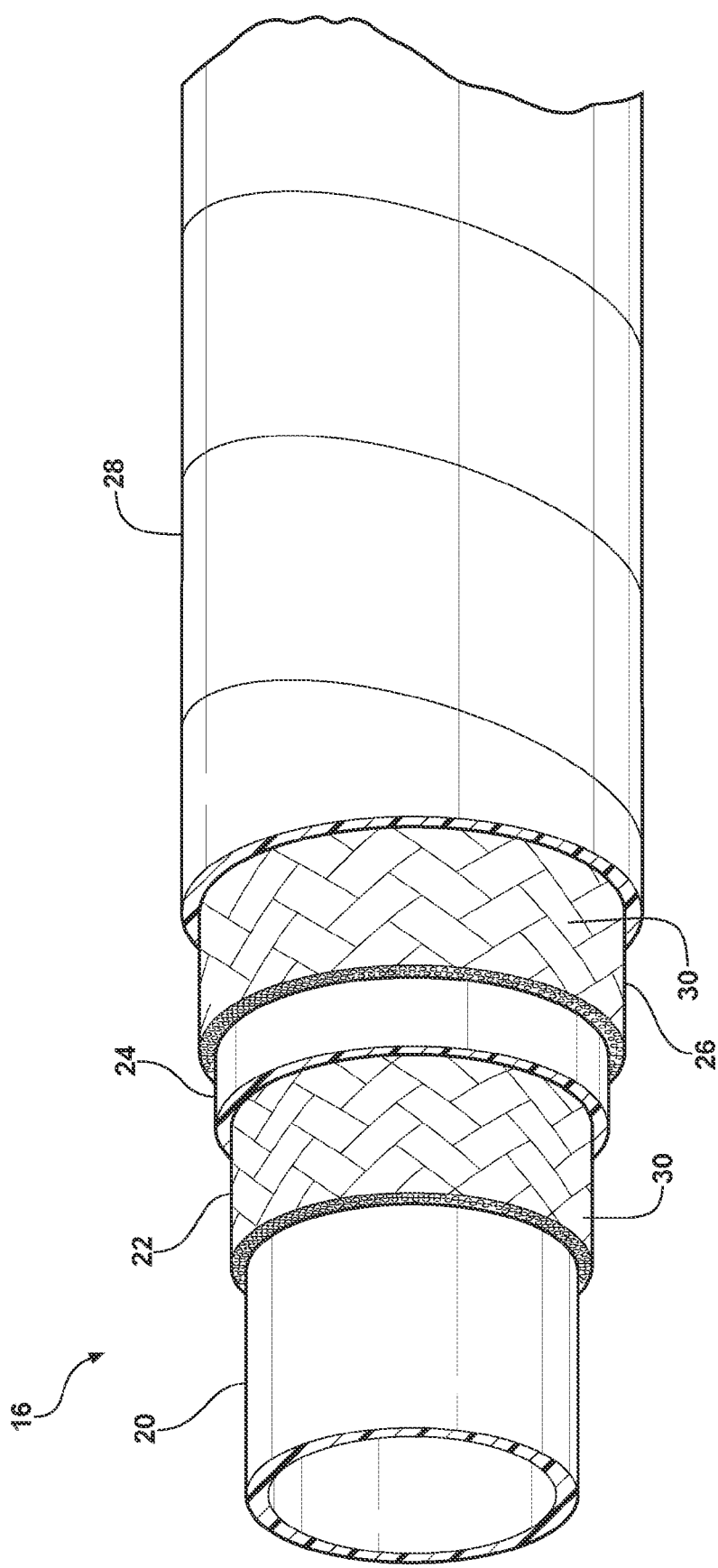
FIG. 2 is a perspective view, partially cut away, illustrating the exemplary hose employing a braided reinforcement layer.

Referring also to FIGS. 2 and 3, the first and second conductive layers 22, 26 may include, for example, an electrically conductive braided reinforcement material 30, such as shown in FIG. 2, or alternating layers of electrically conductive spiral reinforcement material 32, such as shown in FIG. 3. The braided reinforcement material 30 may include a single layer or may include multiple layers. Although a two-wire spiral reinforcement arrangement is depicted in FIG. 3, it shall also be appreciated that other configurations, such as four and six wire arrangements, may also be utilized.

The conductive layers 22, 26 may each have the same configuration, or each layer 22, 26 may be configured differently. For example, the first and second conductive layers 22, 26 may each include the braided material shown in FIG. 2, or one layer may include the braided reinforcement material 30 and the second conductive layer 26 may include the spiral reinforcement material 32 shown in FIG. 3. Additionally, the first and second conductive layers 22, 26 may include a single ply or multiple plies of reinforcement material 22, 26. The first and second conductive layers 22, 26 may include metal wire, natural or synthetic fibers and textiles, and other reinforcement materials, provided the selected material is electrically conductive. The use of the terms "first" and "second" used to describe the conductive layers 22, 26 is not intended to limit or otherwise dictate the position or placement of the conductive layers 22, 26 within the hose assembly 12.

The hose assembly 12 may include a nipple 36 that engages the inside of the hose 16 and a socket 40 that engages an outer surface 41 of the hose 16. The nipple 36 may include an elongated cylindrical end portion 42 that engages an inner surface 43 of the hose 16. It should be appreciated that in the embodiments shown in FIGS. 1 and 5-9, the nipple 36 engages the inner surface 43 of the inner tube 20 of the hose 16. A cylindrically shaped end portion 44 of the socket 40 may engage the outer cover 28 of the hose 16. The socket 40 and nipple 36 may be constructed from an electrically conductive material. The socket 40 and nipple 36 may be secured to the hose 16 by crimping the cylindrically shaped end portion 44 of the socket 40 overlaying the hose 16. The crimping process deforms the cylindrically shaped end portion 44 of the socket 40, thereby compressing the hose 16 between the nipple 36 and the socket 40. The portions of the nipple 36 and the socket 40 that engage the hose 16 may also include a series of serrations 46 that at least partially embed into the relatively softer hose material when the socket 40 is crimped to help secure the fitting to the hose 16. The serrations 46 may be configured to prevent the serrations 46 from penetrating the inner tube 20 and outer cover 28 and contacting the conductive layers 22, 26.

Figure 5:
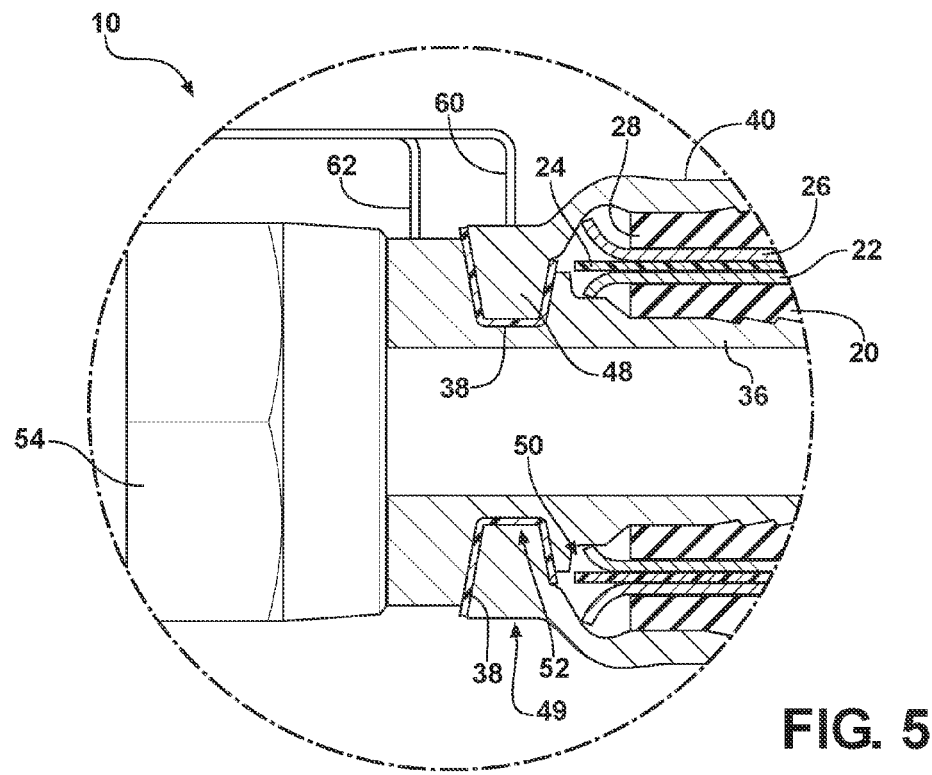
FIG. 5 is an exploded partial cross-sectional view of a portion of the exemplary hose illustrating a connection scheme for attaching the reinforcing layers to a socket and a nipple.
Figure 7:
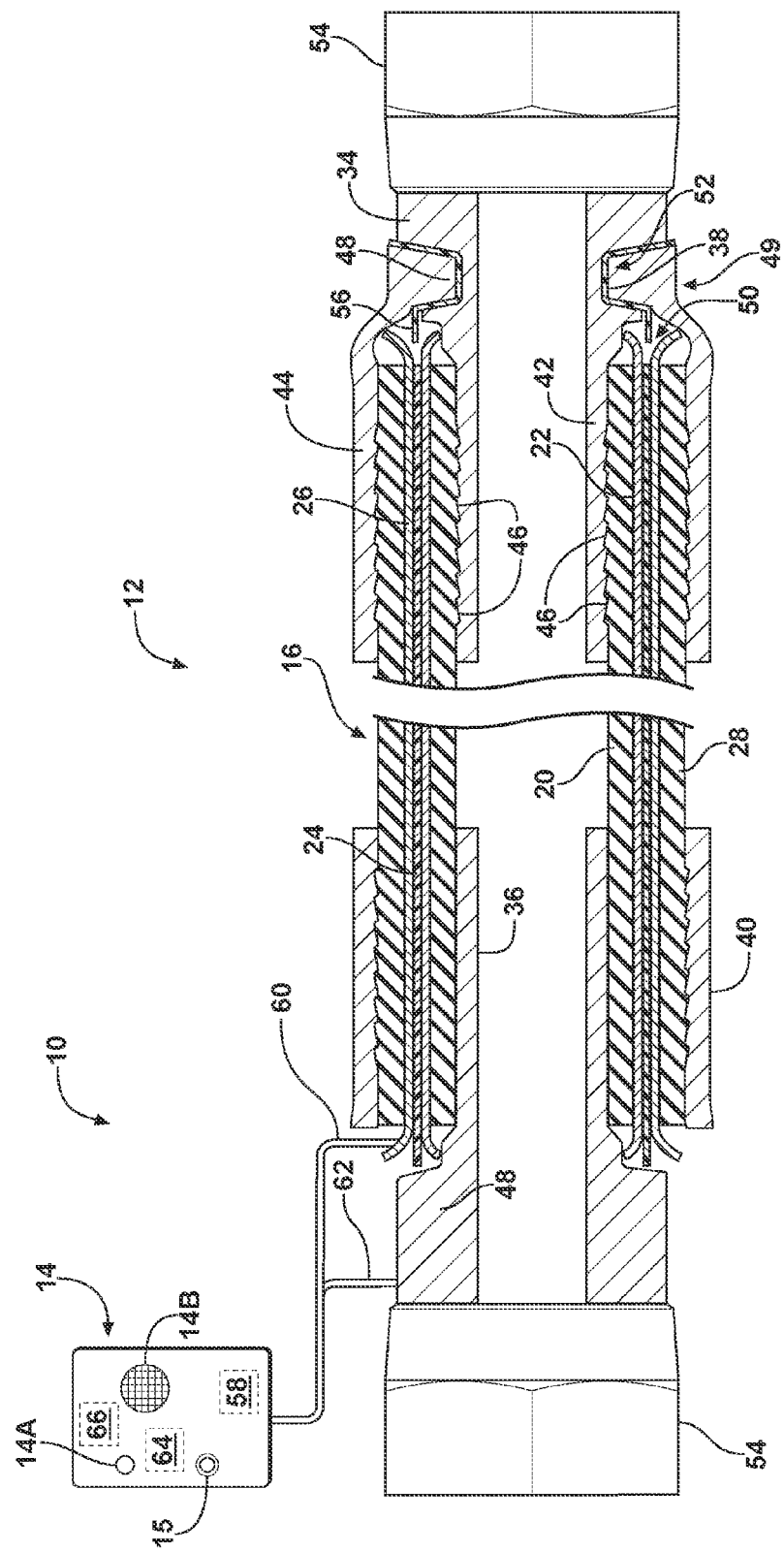
FIG. 7 is a partial cross-sectional view of the exemplary hose of FIG. 1 employing a modified socket and nipple.

Referring to FIGS. 1, 5, and 7, the socket 40 and the nipple 36 may also be secured to one another in addition to being secured to the hose 16. The socket 40 may include an inwardly extending circumferential lug 48 positioned near a deformable end 49 of the socket 40, adjacent a hose end 50 of the hose. The lug 48 engages a corresponding circumferential slot 52 formed in the nipple 36. The deformable end portion 49 of the socket 40 having the lug 48 may initially be formed larger than the nipple 36 to enable the socket 40 to be assembled onto the nipple 36. During the assembly process the deformable end portion 49 of the socket 40 is crimped, which deforms the socket 40 and forces the lug 48 into engagement with the corresponding slot 52 in the nipple 36. The socket 40 can be electrically insulated from the nipple 36 by positioning an electrically insulating collar 38 between the socket 40 and nipple 36 at the point the lug engages the slot.

Referring to FIGS. 1 and 5-9, a nut 54 may be rotatably attached to the nipple 36. The nut 54 is configured to secure the hose assembly 12 to another component (not shown).

Referring to FIGS. 1 and 5-7, the first conductive layer 22 may be configured to extend beyond an end of the inner tube 20 of the hose 16. The first conductive layer 22 may engage the nipple 36 to create an electrical connection between the nipple 36 and the first conductive layer 22. Similarly, referring to FIGS. 1, 5, and 7, the second conductive layer 26 may be configured to extend beyond an end of the outer cover 28 of the hose 16. The second conductive layer 26 may engage the socket 40 to create an electrical connection between the socket 40 and the second conductive layer 26.

Figure 6:
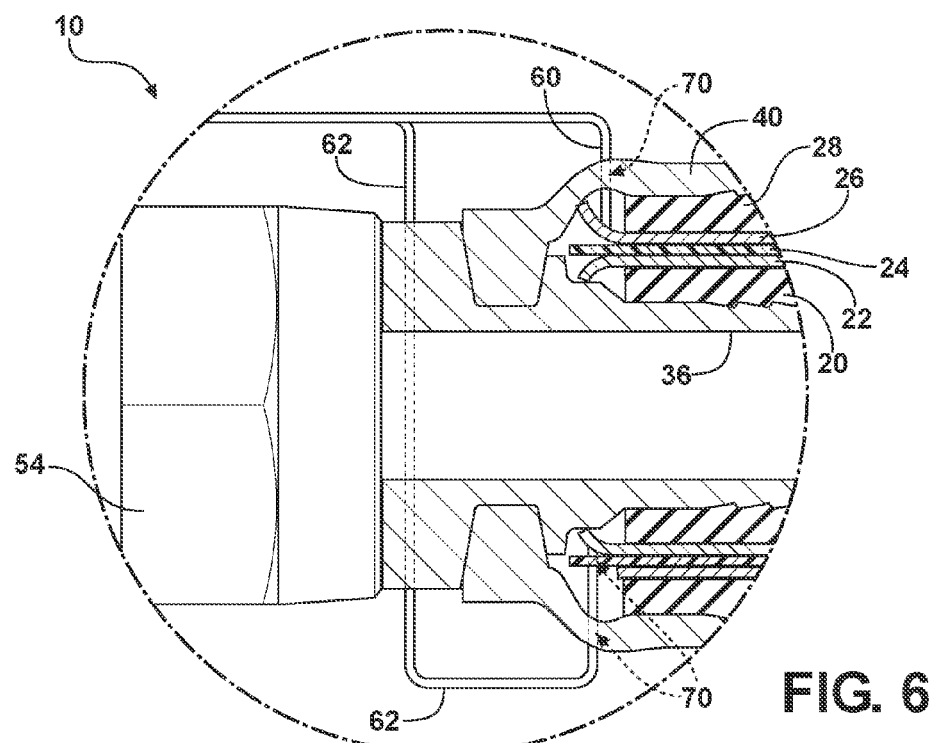
FIG. 6 is an exploded partial cross-sectional view of the exemplary hose illustrating a connection scheme for connecting a fault detector to the reinforcing layers.

Referring again to FIGS. 1 and 7, to help prevent the portions of the first and second conductive layer 22, 26 that extend beyond the end of the hose 16 from contacting one another, an electrically insulating spacer 56 may be positioned between exposed ends of the first and second conductive layer 22, 26. The spacer 56 may be integrally formed as part of the collar 38 used to electrically insulate the socket 40 from the nipple 36. The spacer 56 may also be formed by extending the hose intermediate layer 24 beyond an end of the inner tube 20 and outer cover 28, as shown in FIG. 6. The spacer 56 may also be configured as a stand-alone component, separate from the collar 38 and the intermediate layer 24 of the hose 16.

The hose fault detection system 10 may include the fault detector 14 for monitoring the integrity of the hose 16. The fault detector 14 may be configured to cause a notification signal to be generated when a fault is detected within the hose 16. The notification signal may include audible and visual signals, as well as other types of signals. This means that the fault detector 14 may include a visual fault indicator 14A that corresponds to the visual signals and/or an audio fault indicator 14B that corresponds to the audio signals. Additionally, the fault detector 14 may include a reset button 15.

Figure 8:
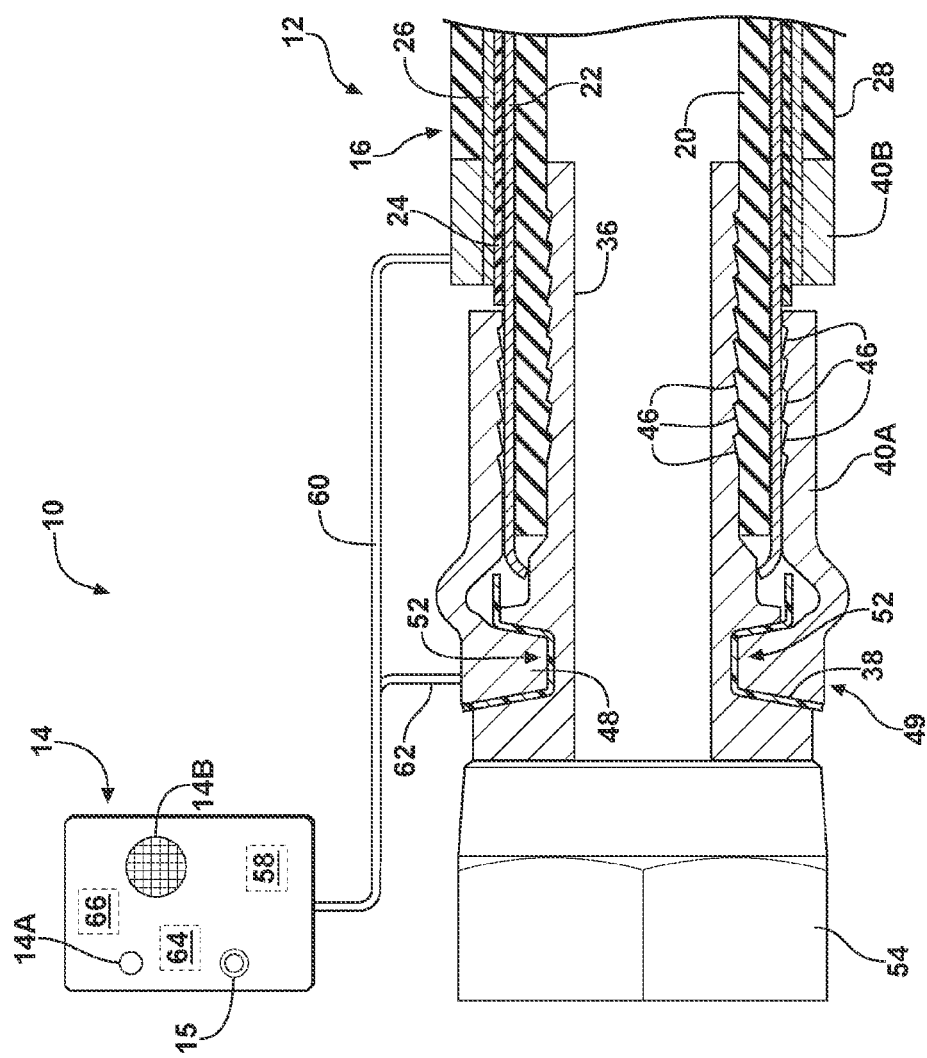
FIG. 8 is a partial cross-sectional view of another exemplary hose of FIG. 1 employing a modified socket and nipple.

Referring to FIGS. 1, 7, and 8, the fault detector 14 may have any of a variety of configurations depending on the electrical characteristic being monitored, such as resistance and capacitance. For example the fault detector 14 may include a sensing device 58 capable of measuring the desired electrical characteristic. The sensing device 58 may be electrically connected to the first and second conductive layer 22, 26 by way of first and second lead wire 60, 62 that are electrically connected to the socket 40 and nipple 36, respectively. The first and second conductive layers 22, 26 may also be electrically connected to the nipple 36 and socket 40, respectively, thus enabling the fault detector 14 to monitor the electrical properties of the conductive layers 22, 26. The fault detector 14 may also include a recording device 64 for storing measured electrical property data. A digital processor 66 may also be employed with the fault detector 14 for performing various calculations and manipulations of the received electrical property data as may be required based on the electrical property being monitored and the requirements of the particular application.

A method for determining the presence of a fault within the hose 16 may include monitoring an electrical property of at least one of the first and second conductive layer 22, 26, including but not limited to, electrical resistance and capacitance. An impending fault occurring within the hose 16 may produce a detectable change in the monitored electrical property, which may indicate that a hose failure is about to occur.

There are a wide variety of mechanisms by which a hose 16 failure may occur. A hydraulic hose 16 may be subjected to cyclic pressure changes that may result in a progressive fatigue induced degeneration of one or more of the layers within the hose 16, which typically precedes a complete failure of the hose. For purposes of discussion, a complete failure of the hose 16 occurs when an opening develops in a wall of the hose 16 that allows fluid to escape from the hose 16. The ability to detect degeneration occurring within the hose 16 may provide an opportunity to remove the hose 16 from service prior to a complete failure.

Progressive hose 16 degeneration may produce a corresponding detectable change in the electrical characteristics of the conductive layers 22, 26 which, when detected, may forewarn of an impending complete hose 16 failure. For example, if the intermediate layer 24 of the hose 16 were to develop a tear 68 or other similar fault that results in the first conductive layer 22 electrically contacting the second conductive layer 26, such as shown in FIG. 4, this may in turn cause a corresponding decrease in electrical resistance between the two conductive layers 22, 26 that can be detected by the fault detector 14. It may also be possible that fibers or wires of one of the conductive layers 22, 26 could begin to fray. This may be characterized by the breakage of individual wires within the respective conductive layer 22, 26 in instances where the conductive layer 22, 26 is constructed from a braided material, such as shown in FIG. 2. One or more of the frayed wires may pierce the intermediate layer 24 and contact the other conductive layer 22, 26, resulting in a corresponding decrease in electrical resistance between the two layers, i.e., an "electrical short". Further, a change in the physical relationship between the two conductive layers 22, 26, such as may occur due to swelling of the hose that may be caused by fluid entering one or more of the hose layers 20, 22, 24, 26, 28 through an interior fault in the hose 16, may produce a corresponding change in capacitance. Upon detecting a change in the monitored electrical characteristic, the fault detector 14 can cause visual and audio signals to be broadcast signaling the presence of a fault within the hose 16.

Various methods may be used to determine the presence of a fault within the hose 16. For example, a newly constructed hose 16 may have an initial baseline electrical characteristic. This baseline electrical characteristic may be preprogrammed into the fault detector 14, or the fault detector 14 may be configured to perform an initial measurement to establish the baseline electrical characteristic. Once the baseline electrical characteristic has been established, the fault detector 14 may continuously or periodically send out a predetermined signal consistent with the electrical characteristic being monitored. A return signal received by the fault detector 14 may be used to determine the current electrical characteristics of the hose, which may be compared against the baseline electrical characteristic. Changes exceeding a predetermined magnitude may indicate an impending hose 16 failure for which the fault detector 14 can cause of warning to be issued.

Rather than comparing the currently measured electrical property with a baseline property, the fault detector 14 may also be configured to issue an impending hose failure warning upon the monitored electrical property attaining, exceeding or falling below a certain value. For example, when monitoring electrical resistance, the fault detector 14 may be configured to issue a warning when the electrical resistance falls below a certain level.

Referring also to FIG. 6, the first and second lead wires 60, 62 of the fault detector 14 may be connected directly to the corresponding conductive layers 22, 26 rather than the socket 40 and nipple 36. The first and second lead wires 60, 62 of the fault detector 14 can be routed through a respective hole 70 in the socket 40 and electrically attached to the corresponding conductive layers 22, 26, such as by soldering and the like. To prevent the exposed ends of the conductive layers 22, 26 from contacting one another, the hose intermediate layer 24 may be extended beyond the end of the hose inner tube 20 and the hose outer cover 28. The first lead wire 60 may be attached to the first conductive layer 22 by being routed through a hole 70 in the intermediate layer 24 or around an end of the intermediate layer 24. Each lead wire 60, 62 may be routed through its own individual hole 70 in the socket 40, as illustrated in FIG. 6, or the lead wires 60, 62 may be routed through a common hole 70. Because the first and second lead wires 60, 62 are connected directly to the respective first and second conductive layers 22, 26, it may be possible to do away with the collar 38 that is positioned between the socket 40 and the nipple 36 since it is not necessary to electrically insulate the socket 40 from the nipple 36.

With reference to FIG. 7, the socket 40 may be configured as a cylindrically shaped sleeve. The socket 40 engages the outer cover 28 of the hose 16 in a similar manner as the socket 40 shown in FIG. 1. The socket 40 generally does not extend beyond an end of the outer cover 28. This may enable easy access to the conductive layers 22, 26 to facilitate connecting the fault detector 14 lead wires 60, 62 to the respective conductive layers 22, 26, and may also simplify routing of the lead wires 60, 62. The socket 40 may be secured to the hose 16 by crimping the portion of the socket 40 overlaying the hose 16.

Referring to FIG. 8, the socket 40 may be configured as a first and a second socket member 40A, 40B. One of the socket members 40A, 40B electrically engages the first conductive layer 22 and the other socket member 40B electrically engages the second conductive layer 26. The hose assembly 12 may also include a nipple 36 that engages the inside of the hose 16. The nipple 36 may include an elongated cylindrical end portion 42 that engages the inner tube 20 of the hose 16.

With continued reference to FIG. 8, a socket portion may include the first socket member 40A that mechanically and electrically engages the first conductive layer 22. The first socket member 40A may be constructed from an electrically conductive material. The first socket member 40A and the nipple 36 may be secured to the hose 16 by crimping the deformable end portion 49 of the first socket member 40A overlaying the first conductive layer 22 of the hose 16. The crimping process deforms the deformable end portion 49 of the first socket member 40A, thereby compressing the inner tube 20 and the first conductive layer 22 of the hose 16 between the nipple 36 and the first socket member 40A. The portions of the nipple 36 and the first socket member 40A that engage the hose 16 may include a series of serrations 46 that at least partially embed into the relatively softer hose material when the first socket member 40A is crimped to help secure the fitting 34 to the hose 16. The first socket member 40A is not electrically coupled to the second conductive layer 26. The first lead wire 60 of the fault detector 14 may be electrically connected to the first socket member 40A.

Referring again to FIG. 8, the first socket member 40A and the nipple 36 may be secured to one another in addition to being secured to the hose 16. The first socket member 40A may include the inwardly extending circumferential lug 48 positioned near the deformable end portion 49 of the first socket member 40A, adjacent the end of the hose. The lug 48 engages a corresponding circumferential slot 52 formed in the nipple 36. The deformable end portion 49 of the first socket member 40A having the lug 48 may be initially formed larger than the nipple 36 to enable the first socket member 40A to be assembled onto the nipple 36. During the assembly process the deformable end portion 49 of the first socket member 40A is crimped, which deforms the first socket member 40A and forces the lug 48 into engagement with the corresponding slot 52 in the nipple 36.

It is not necessary that the nipple 36 be electrically insulated from the first socket member 40A since the nipple 36 is not electrically coupled to the second conductive layer 26 of the hose. It may, however, be desirable in certain instances to position the collar 38 between the lug 48 of the first socket member 40A and the nipple 36 for a various reasons, such as to facilitate attachment of the first socket member 40A to the nipple 36. The collar 38 may be made from any of a variety of materials depending on the requirements of the particular application. It is not required that the collar 38 be electrically insulating, although it may be.

Referring again to FIG. 8, the socket 40 portion may also include a second socket member 40B that mechanically and electrically engages the second conductive layer 26. The second socket member 40B may be constructed from an electrically conductive material. The second socket member 40B may be configured as a generally cylindrically shaped sleeve that engages the second conductive layer 26 of the hose 16 in a similar manner as the first socket member 40A engages the first conductive layer 22. The second socket member 40B may be secured to the hose 16 by crimping the portion of the socket 40 overlaying the second conductive layer 26, thereby trapping a portion of the inner tube 20, the first conductive layer 22, the intermediate layer 24, and the second conductive layer 26 between the second socket member 40B and the nipple 36. The second socket member 40B is not electrically connected to the first conductive layer 22. The second lead wire 62 of the fault detector 14 may be electrically connected to the second socket member 40B.

With reference to FIGS. 9 and 10, the inner portion of the socket 40 that engages the hose 16 may be provided with a generally conical shaped region 72, wherein an inner diameter D of the socket 40 tapers progressively inward starting from the end of the socket 40. The taper 74 operates to minimize stress concentration occurring within the hose 16 at the point where the hose 16 exits the socket 40. The taper 74 allows for a gradual increase in the compressive forces being applied to the hose 16 when the socket 40 is crimped on the nipple 36. For example, region A of the socket 40 in FIG. 10 can be provided with a generally conical taper 74, whereas region B may have a generally constant diameter D. When the socket 40 is attached to the hose 16 and crimped to the nipple 36, the compressive forces applied to the hose 16 will increase gradually over region A, starting from the end of the socket 40 and moving inward. The compressive forces will likely reach a maximum within region B. Without the taper 74, for example, if regions A and B were to have generally the same diameter D, the stresses within the hose 16 may increase much more quickly, which in turn could adversely impact the durability of the hose. The taper 74 of the conical shaped region 72 may help minimize this by allowing for a more gradual increase in the compression forces exerted on the hose 16 by the socket 40.

The arrangements described above are merely illustrative examples of possible configurations. It shall be appreciated that the arrangement of the fault detection system 10, as well as the configuration of the individual components, including but not limited to the hydraulic hose 16 and fittings, can have different configurations without departing from the scope of the claimed device. Further, although the above examples focus on a hydraulic hose 16 it shall be understood that the herein describe device may be employed with any hose configured for transporting a fluid or gas.

With regard to the processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain features, and should in no way be construed so as to limit the scope of the claims.

It is to be understood that the above description is intended to be illustrative and not restrictive. Many arrangements and applications other than the examples provided would be apparent to those of skill in the art upon reading the above description. The scope of the disclosed system and processes should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the herein disclosed system and processes are capable of modification and variation and are limited only by the following claims.

What is claimed is:

1. A hose fault detection system comprising:
    a hose including:
        an inner tube;
        a first conductive layer with an electrically conductive characteristic;
        wherein the first conductive layer overlays the inner tube;
        a second conductive layer with an electrically conductive characteristic;
        wherein the second conductive layer surrounds the first conductive layer;
        an outer cover surrounding the second conductive layer;
    a nipple including a plurality of serrations in engagement with the inner tube to secure the nipple to the hose without fully penetrating the inner tube, whereby the plurality of serrations of the nipple do not contact the first conductive layer;
    a socket including a plurality of serrations in engagement with the outer cover to secure the socket to the hose without fully penetrating the outer cover, whereby the plurality of serrations of the socket do not contact the second conductive layer; and
    a fault detector electrically connected to at least one of the first conductive layer and the second conductive layer and configured for detecting an electrical change based on the electrically conductive characteristic to signify a potential impending failure of the hose.

2. The hose fault detection system of claim 1, wherein the at least one conductive layer includes an electrically conductive material.

3. The hose fault detection system of claim 1, wherein the hose further includes an intermediate layer disposed between the first and second conductive layers.

4. The hose fault detection system of claim 3, wherein the intermediate layer is configured to electrically insulate the first conductive layer from the second conductive layer.

5. The hose fault detection system of claim 3 further comprising a socket electrically connected to at least one of the first and second conductive layers, and wherein the fault detector is electrically connected to the socket.

6. The hose fault detection system of claim 3 wherein the nipple is electrically connected to at least one of the first and second conductive layers, and wherein the fault detector is electrically connected to the nipple.

7. The hose fault detection system of claim 3, further comprising a first lead wire electrically interconnecting the fault detector and the first conductive layer and a second lead wire electrically interconnecting the fault detector and the second conductive layer.

8. The hose fault detection system of claim 3,
    wherein the fault detector is electrically connected to the socket and the nipple.

9. The hose fault detection system of claim 8, further including a collar disposed between the socket and the nipple, wherein the collar is configured to electrically insulate the socket from the nipple.

10. The hose fault detection system of claim 9, wherein the collar further includes a spacer disposed between a portion of each of the first and second conductive layers, wherein the spacer is configured to electrically insulate the first conductive layer from the second conductive layer.

11. The hose fault detection system of claim 3, wherein at least one of the first and second conductive layers includes an electrically conductive braided reinforcement material.

12. The hose fault detection system of claim 3, wherein at least one of the first and second conductive layers includes an electrically conductive spiral reinforcement material.

13. A hose fault detection system comprising:
    a hose assembly including;
        an inner tube;
        a first conductive layer,
        wherein the first conductive layer overlays the inner tube,
        a second conductive layer,
        wherein each of the first and second conductive layers has an electrical characteristic,
        an outer cover surrounding the second conductive layer,
        an intermediate layer disposed between the first and second conductive layers,
        a nipple including a plurality of serrations in engagement with the inner tube to secure the nipple to the hose without fully penetrating the inner tube, whereby the plurality of serrations of the nipple do not contact the first conductive layer;
        a socket including a plurality of serrations in engagement with the outer cover to secure the socket to the hose without fully penetrating the outer cover, whereby the plurality of serrations of the socket do not contact the second conductive layer;
    a fault detector electrically connected to at least one of the first conductive layer and the second conductive layer and configured for detecting an electrical change based on the electrical characteristic to signify a potential impending failure of at least one of the first and second conductive layers of the hose, wherein the fault detector includes;
        a sensing device in electrical communication with the first and second conductive layers to measure the electrical characteristic;
        a recording device configured for storing the measured electrical characteristic; and
        a digital processor.

14. A hose fault detection system comprising:
    a hose assembly including;
        an inner tube,
        a first conductive layer,
        wherein the first conductive layer overlays the inner tube,
        a second conductive layer,
        wherein each of the first and second conductive layers has an electrical characteristic,
        an outer cover surrounding the second conductive layer,
        a nipple in electrical communication with the first conductive layer,
        wherein the nipple includes a plurality of serrations in engagement with the inner tube to secure the nipple to the hose without fully penetrating the inner tube, whereby the plurality of serrations of the nipple do not contact the first conductive layer,
        a socket in electrical communication with the second conductive layer,
        wherein the socket includes a plurality of serrations in engagement with the outer cover to secure the socket to the hose without fully penetrating the outer cover, whereby the plurality of serrations of the socket do not contact the second conductive layer,
    a fault detector configured for detecting an electrical change based on the electrical characteristic to signify a potential impending failure of at least one of the first and second conductive layers of the hose, wherein the fault detector includes;
a sensing device configured to measure the electrical characteristic between the first and second conductive layers;
a first lead wire electrically interconnecting the sensing device and the socket; and
a second lead wire electrically interconnecting the sensing device and the nipple.

* * * * *